United States Patent [19]

Long et al.

[11] 3,960,843

[45] June 1, 1976

[54] PROCESS FOR THE PREPARATION OF ESTERS OF N-BLOCKED PENICILLIN ACIDS WHICH COMPRISES REACTING THE ACID OR A SALT THEREOF WITH A PRIMARY AMINE AND A NITROSATING AGENT

[75] Inventors: Alan Gibson Long, Greenford; Derek Walker, Windermere; David Thomas Eastlick, Scotforth; Harry Carson Stables, Ulverston, all of England

[73] Assignee: Glaxo Laboratories Limited, Greenford, England

[22] Filed: July 9, 1973

[21] Appl. No.: 377,268

[52] U.S. Cl. .................. 260/239.1; 260/243 C; 424/271; 424/246

[51] Int. Cl.$^2$ .............. C07D 499/08; C07D 501/02
[58] Field of Search ................ 260/243 C, 239.1

[56] References Cited
UNITED STATES PATENTS
3,284,451  11/1966  Cheney et al. .................. 260/243 C

*Primary Examiner*—Nicholas S. Rizzo
*Attorney, Agent, or Firm*—Bacon & Thomas

[57] ABSTRACT

A process is described for the preparation of esters of N-blocked amino acids (such as penicillins or cephalosporins) wherein the amino acid or a salt thereof is reacted with a primary amine and nitrosating agent.

6 Claims, No Drawings

PROCESS FOR THE PREPARATION OF ESTERS OF N-BLOCKED PENICILLIN ACIDS WHICH COMPRISES REACTING THE ACID OR A SALT THEREOF WITH A PRIMARY AMINE AND A NITROSATING AGENT

This invention is concerned with improvements in or relating to the preparation of esters of N-blocked amino acids.

There is a growing need for esterification processes which can be applied to such acids without disturbing their molecular geometry, i.e. without molecular disruption or molecular rearrangements such as isomerization and racemization. Such processes are particularly needed in the manufacture of cephalosporin and penicillin antibiotics where it is frequently necessary to protect a carboxyl group by esterification to enable chemical transformations to be carried out elsewhere in the molecule.

Esterification of penicillin and cephalosporin compounds is beset with difficulties owing to the facility with which a variety of undesired side reactions can occur. For example:

1. The β-lactam ring may open easily under quite mild conditions. Also, in the presence of acids, undesired reaction can occur between the secondary amide group and the β-lactam ring, especially in the penicillins.

2. Furthermore, in the presence of acids, the 4-carboxyl group in cephalosporins containing various functional groups at C-3, e.g. $CH_2OH$ or $CH_2OCOCH_3$, can easily undergo γ-lactone ring formation.

3. Additionally, the carboxyl group of both penicillins and cephalosporins can enter into reactions. For example, in ester forming reactions in the presence of base, the penicillins may rearrange to anhydro-penicillins and cephalosporins may give mixtures of 2-em and 3-em products.

It may be necessary to remove the carboxyl-protecting group from penicillins and cephalosporins after the desired chemical transformation has been accomplished. This leads to the further need that the carboxyl-protecting group should be of such a structure that it can be easily removed later in the process under mild conditions. Protecting groups of this type include diphenylmethyl and p-methoxybenzyl.

On account of these difficulties, the generally useful and cheap esterifying methods are of limited value for the esterification of N-blocked amino acids, such as penicillins and cephalosporins, for protective purposes.

We have now found that a variety of esters can conveniently be obtained under mild conditions by using as the esterifying agent a combination of a primary amine and a nitrosating agent. Esterification using such an agent is particularly applicable to N-blocked amino acids containing a β-lactam structure, e.g. penicillin and cephalosporin acids, as well as to other N-blocked amino acids and N-blocked peptides.

According to one embodiment of the present invention there is provided a process for the preparation of an ester of an N-blocked amino acid which comprises reacting the N-blocked amino acid, or a salt thereof, with an amine of formula $RNH_2$ (where R is an organic group e.g. a hydrocarbyl group) and a nitrosating agent to yield an N-blocked amino acid ester in which the ester group has the formula -COOR (where R has the above defined meaning).

When a salt of the N-blocked amino acid is used, this may be a salt with either the amine $RNH_2$ or with another base (e.g. an alkali metal salt, e.g. a potassium or lithium salt). These salts, and particularly those formed with an amine, may be preformed and it is not of course necessary to effect their formation in the presence of the nitrosating agent. One may thus for example react a salt formed from the amine and the N-blocked amino acid with a nitrosating agent.

The resulting esters may thus be depicted as having the formula Q.COOR (where R has the above defined meaning and Q.COOH is the N-blocked amino acid). Q may be a group containing 1 – 50 carbon atoms. The acid may be a mono-, di- or polycarboxylic acid.

The group R advantageously contains 1 – 30 carbon atoms, more preferably 5 – 20 carbon atoms. Thus R may be selected from, for example, cycloalkyl groups containing 5 – 7 carbon atoms in the ring, e.g. cyclopentyl or cyclohexyl; aralkyl groups containing 1 -3, preferably 1 or 2 aryl groups, said aryl groups preferably being attached to the C-1 carbon atom of a lower ($C_{1-6}$) alkyl portion, e.g. benzyl, diphenylmethyl, trityl, 9-fluorenyl, 9 -xanthydryl etc.; heterocyclic substituted lower alkyl groups wherein the alkyl portion carries one or more 5- or 6-membered heterocyclic rings containing one or more of O, N and S, e.g. 2-thienylmethyl or 2-furylmethyl; or any of the above groups carrying one or more substituents selected from halo, e.g. chloro or bromo; cyano; nitro; lower alkyl, e.g. methyl, ethyl, or n-propyl; lower alkoxy, e.g. methoxy, ethoxy, or isopropoxy; lower alkoxycarbonyl, e.g. methoxycarbonyl; and lower alkylsulphonyl, e.g. methylsulphonyl. The lower alkyl and alkoxy groups just referred to may have 1 – 6 carbon atoms.

As indicated above it is particularly desirable to esterify the N-blocked amino acid with an esterifying group R which can subsequently be readily removed under mild conditions, and the amine $RNH_2$ is thus preferably chosen to introduce such a group. Suitable amines thus include diphenylmethylamine; ring-substituted diphenyl-methylamines, e.g. di)o-methylphenyl) methylamine, di(p-methoxyphenyl) methylamine; benzylamine; ring-substituted benzylamines, e.g. p-nitrobenzylamine and lower alkoxy ($C_{1-6}$) benzylamines such as p-methoxybenzylamine; 9-aminofluorene; and heterocyclic alkylamines such as 2-furfurylamine.

The process of the invention is in general preferably applied to the preparation of esters wherein R is an alkyl (e.g. methyl) group substituted by at least one aromatic carbocyclic or aromatic heterocyclic group.

The nitrosating agent may be any compound serving as a source of nitroso groups and will in general be a compound of formula NOX where X is an organic or inorganic anion or a group $OR^2$ where $R^2$ is an organic group. X may thus be an organic anion derived from a carboxylic acid, e.g. an alkane carboxylic acid containing 2 – 7 carbon atoms, nitrosating agents of this type including acetyl nitrite and propionyl nitrite. Where X is an inorganic anion this may be derived from, for example, a mineral acid, e.g. a halide ion such as chloride or bromide or a sulphate ion, or from a Lewis acid, e.g. a borofluoride ion. Other inorganic anions include hydroxide and sulphonate. Nitrosating agents of this type thus include nitrosyl chloride, nitrosyl sulphate, nitrosyl borofluoride, nitrous acid and Fremys salt (potassium nitrosyldisulphonate). Where X is a group of formula $OR^2$ the organic group $R^2$ may be, for example, a lower alkyl group preferably containing 1 – 9 carbon atoms, e.g. ethyl, n-propyl, isopropyl, n-butyl, t-butyl or isopentyl. Suitable nitrosating agents of this type thus include isopropyl nitrite, isobutyl nitrite, isoamyl nitrite and t-butyl nitrite.

The esterification is desirably effected in an organic solvent or a mixture of solvents. The organic solvent is advantageously but not necessarily inert. Organic solvents which may be used include chlorinated hydrocarbons, e.g. methylene chloride, chloroform, 1,1-dichloroethane and 1,2-dichloroethane; ethers and cyclic ethers, e.g. diethylether, dioxan and tetrahydrofuran; aromatic hydrocarbons, e.g. benzene and toluene; aliphatic esters e.g. ethyl acetate and butyl acetate; ketones e.g. acetone; amides e.g. dimethylformamide and dimethyl-acetamide; aliphatic nitriles, e.g. acetonitrile; alkyl nitrites, e.g. isopropyl nitrite; alcohols e.g. methanol and butanol; and sulphoxides e.g. dimethylsulphoxide. Alcohols react with nitrosyl chloride and thus are preferably not used with this nitrosating agent. Alternatively, but less satisfactorily, the reaction may be effected in an aqueous reaction medium, preferably a mixture of water and an organic solvent, e.g. a water immiscible organic solvent such as chloroform. The material to be esterified should be at least partly soluble in the chosen solvent.

The esterification may conveniently be effected at a temperature in the range −50° to +100°C, e.g. −30° to −100°C. Temperatures of +10° to 75°C are preferred with weak nitrosating agents (e.g. isopropyl nitrite) and −30° to +20° with strong nitrosating agents (e.g. nitrosyl chloride). Reaction times will depend on, inter alia, the reaction temperature and the reactivity of the amine $RNH_2$, but are normally in the range 15 minutes – 24 hours.

The course of the esterification may be monitored by following the evolution of nitrogen which occurs during the reaction. In general it is preferred to use an excess of the esterifying agent, e.g., when alkyl nitrites are used as nitrosating agent, 1–3, preferably about 1.75, moles of amine and 1–5, preferably about 3.5, moles of nitrosating agent per mole of N-blocked amino acid. When reactive nitrosating agents such as nitrosyl chloride are used, 1–4, preferably about 2.5, moles of amine and 1–4, preferably about 2.5, moles of nitrosating agent may for example be used per mole of N-blocked amino acid. Cessation of gas evolution under such conditions normally corresponds to termination of the esterification. The reaction may also be monitored using thin layer chromatography or electrophoresis.

The reaction components may be brought together in a number of different ways. For example, in the case of alkyl nitrites, the amine and the nitrosating agent may be brought together in an appropriate solvent and subsequently contacted with the N-blocked amino acid.

An alternative method is to premix the N-blocked amino acid and the amine, yielding a salt of formula $Q.COONH_3R$ (where Q and R are as hereinbefore defined), which salt is subsequently reacted with the nitrosating agent to promote esterification. Similarly the N-blocked amino acid (preferably in the form of a salt) may be premixed with the nitrosating agent and the product subsequently treated with the amine.

The process according to the invention is generally useful for the esterification of N-blocked amino acids and peptides. It is particularly valuable for esterifying the carboxyl group or groups in intermediate compounds encountered in the production of synthetic or semi-synthetic biologically active compounds such as β-lactam antibiotics.

The process of the invention is especially suitable when a sulphur atom is present in the N-blocked amino acid as the sulphur will usually be unaffected by the reagents used. For example, in the manufacture of cephalosporin and penicillin antibiotics it is frequently necessary to protect a carboxyl group in a carboxyl group-containing ring system by esterification to enable chemical transformation to be carried out elsewhere in the molecule. An important example of this lies in the ring expansion process for manufacturing cephalosporin antibiotics from penicillin compounds, as disclosed, for example, in Belgian Pat. Nos. 747,118; 747,119 and 747,120.

The penicillin and cephalosporin compounds referred to in this specification are generally named with reference to cepham (J. Amer. Chem. Soc. 1962, 84, 3400) and penam (J. Amer. Chem. Soc. 1953, 75, 3293). The term "cephem" refers to the basic cepham structure with one double bond.

Thus N-blocked amino acids which may be esterified by the process according to the invention include penicillin and cephalosporin compounds corresponding to the skeletal formula

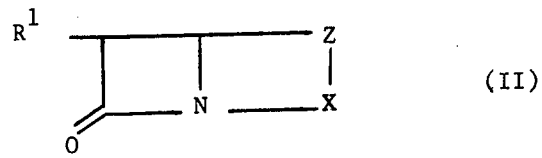
(II)

wherein Z is >S or >S → O (α- or β-); X is a divalent group selected from

(a)

and

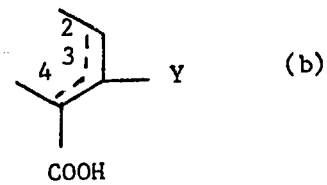
(b)

(where Y is methyl; substituted methyl e.g. — $CH_2Y'$ where Y' is the residue of a nucleophile, including such groups as acetoxy, hydroxy or carbamoyloxy; or an unsaturated group such as vinyl or substituted vinyl and the dotted line between the 2-, 3- and 4-positions of (b) indicates that the compound may be a ceph-2-em or ceph-3-em compound) and $R^1$ is a blocked amino group e.g. a carboxylic acylamido group (e.g. containing 1–20 carbon atoms) or a protonated amino group ($NH_3^+$). The invention finds particular application where Z is >S.

Where $R^1$ is a carboxylic acylamido group this may be chosen from the extensive lists of such acyl groups in the penicillin and cephalosporin literature. Specific acyl groups are illustrated in the accompanying list which is not intended to be exhaustive:

i. $R^u C_n H_{2n} CO-$ where $R^u$ is aryl (carbocyclic or heterocyclic), cycloalkyl, substituted aryl, substituted cycloalkyl, cycloalkadienyl, or a non-aromatic heterocyclic or mesoionic group and $n$ is O or an integer from 1–4. Examples of this group include phenylacetyl; thien-2- and -3-ylacetyl; 4-isoxazolyl and 4-isoxazolylacetyl both substituted or unsubstituted; pyridylacetyl, tetrazolylacetyl or a sydnoneacetyl group.

ii. $C_n H_{2n+1} CO-$ where $n$ is O or an integer from 1–7. The alkyl group may be straight or branched and may be substituted by e.g. a cyano group, a carboxy group, an alkoxycarbonyl group, a hydroxy group, an amino group or carboxycarbonyl group (—CO.COOH) or any such group in which the functional group is blocked. Examples of such groups include formyl, glutaronyl, δ-aminoadipoyl and N-benzoyl-δ-aminoadipoyl.

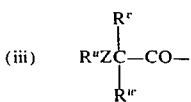

(iii)  $R^u Z \overset{R^v}{\underset{R^w}{C}} - CO-$ where $R^u$ has the meaning defined under (i) and in addition may be benzyl, and $R^v$ and $R^w$ which may be the same or different each represent hydrogen, phenyl, benzyl, phenethyl or lower alkyl and Z is an oxygen or sulphur atom. Examples of this group include phenoxyacetyl or pyridylthioacetyl.

iv. Hydrocarbyloxycarbonyl and substituted hydrocarbyloxy groups (wherein the 6-or 7-amino group forms part of a urethane), in particular lower alkoxycarbonyl groups (such as methoxycarbonyl, ethoxycarbonyl and, most preferably, t-butoxycarbonyl groups); halo lower alkoxycarbonyl groups e.g. 2,2,2-trichloroethoxycarbonyl; aralkoxycarbonyl groups such as benzyloxycarbonyl, 4-methoxybenzyloxycarbonyl, diphenylmethoxycarbonyl and 4-nitrobenzyloxycarbonyl groups. Cycloalkoxycarbonyl groups are also advantageous, especially the adamantyloxycarbonyl group.

v. $R^u.CH(X).CO-$ where $R^u$ has the meaning defined under (i) and X is amino, substituted amino (e.g. acylamido or a group obtained by reacting the α-aminoacylamido group of the 6-or 7-side chain with an aldehyde or ketone e.g. acetone, methylethylketone or ethyl acetoacetate), hydroxy, carboxy, esterified carboxy, azido, triazolyl, tetrazolyl, cyano, halogeno, acyloxy (e.g. formyloxy or lower alkanoyloxy) or etherified hydroxy group. Examples of such acyl groups are α-aminophenylacetyl, and α-carboxyphenylacetyl. It will be appreciated that, when X is amino, this group will normally be blocked before an acid containing this particular acyl group can be used in our process.

It will be appreciated that skeletal formula II includes within its structure compounds not specifically embraced by groups (a) and (b), e.g. 2β-acetoxymethylpenicillins, 2-methyl and 2-methylene cephalosporins, 6α-methoxypenicillins and 7α-methoxycephalosporins.

Compounds of formula (IIb) wherein Y' is the residue of a nucleophile may be prepared by reacting the compound of formula (IIb) where Y' is acetoxy with a nucleophile, for example pyridine or other tertiary amine as described in British Pat. No. 912,541; a sulphur-linking, nitrogen-linking or inorganic nucleophile as described in British Pat. No. 1,012,943; a sulphur-linking nucleophile as described in British Pat. No. 1,059,562; a nitrogen-linking nucleophile as described in British Pat. Nos. 1,030,630, 1,082,943 and 1,082,962; or a sulphur-linking nucleophile as described in British Pat. Nos. 1,101,423 and 1,206,305. This list is not limiting and is given purely by way of illustration.

Compounds of formula (IIb) where Y' is a hydroxy group may be prepared by the methods described in British Pat. No. 1,121,308; compounds in which Y' is a carbamoyloxy group are described in Belgian Pat. No. 764,160.

Where Y in formula (IIb) is a methyl group the compound may be prepared by the method described in British Pat. No. 957,569.

The following Examples serve to illustrate the invention. All temperatures are in °C. "t.l.c" refers to thin layer chromatography.

EXAMPLE 1

Diphenylmethyl 3-acetoxymethyl-7β-(2-Thienylacetamido)ceph-3-em-4-carboxylate

3-Acetoxymethyl-7β-(2-thienylacetamido)ceph-3-em-4-carboxylic acid (3.96 g, 10 m.moles) was dissolved in acetonitrile (50 ml) and dimethylacetamide (5ml). To this solution was added a mixture of isopropyl nitrite (2.4 g, 27 m.moles) and diphenylmethylamine (2.21 g, 12 m.moles) dissolved-suspended in acetonitrile (20 ml). The resulting slurry was stirred for 3 hours at 35°, after which time a solution resulted. The solvents were removed in vacuo and the gum redissolved in chloroform (50 ml). The resulting solution was washed with 5% sodium bicarbonate solution (50 ml), then water (50 ml) and the chloroform removed in vacuo. The gum was crystallised from hot isopropyl alcohol (28 ml), the crystals washed with cold isopropyl alcohol (25 ml) and then dried in vacuo at room temperature to give the title compound. Yield 3.19 g (56.8% based on the input acid); m. pt. and mixed m. pt. 140° – 140.5° with an authentic sample of the ester. The bicarbonate extract was washed with ethyl acetate (10 ml) and then acidified with 2N sulphuric acid at 5° to pH 1.2. The suspension was stirred for 30 minutes, filtered and washed with cold water (70 ml). The recovered starting material was dried in vacuo at room temperature, (0.9 g, single spot on t.l.c. by u.v. detection).

The recovery of some of the starting material gave a corrected yield of 73.5% of diphenylmethyl ester.

EXAMPLE 2

Diphenylmethyl 6β-phenoxyacetamido-2,2-dimethylpenam-3α-carboxylate

6β-Phenoxyacetamido-2,2-dimethylpenam-3α-carboxylic acid (3.50 g, 10 m.moles) was added to a mixture of isopropyl nitrite (2.40 g, 27 m.moles) and diphenylmethylamine (2.21 g, 12 m.moles) in tetrahydrofuran (50 ml) at 35° and stirred for 3 hours. The solvent was removed in vacuo and the gum dissolved in chloroform (50 ml), which solution was washed with 5% sodium bicarbonate solution (50 ml) and then water (50 ml) to leave a gum of the title ester. Yield 2.11 g (40.8% based on the input penicillin acid).

EXAMPLE 3

Diphenylmethyl 6β-phenylacetamido-2,2-dimethylpenam-3α-carboxylate 1β-oxide

6β-Phenylacetamido-2,2-dimethylpenam-3α-carboxylic acid 1β-oxide (3.50 g, 10 m.moles) was added to a mixture of isopropyl nitrite (2.40 g, 27 m.moles) and diphenylmethylamine (2.21 g, 12 m.moles) and tetrahydrofuran (50 ml) and stirred at 35° for 2 hours. The solvent was evaporated, chloroform (50 ml) added to the gum and the resulting solution washed with 5% sodium bicarbonate solution (50 ml) and then water (30 ml). After removal of the chloroform the gum was crystallised from hot isopropyl alcohol (25 ml) to give the title compound. Yield 3.33 g (64.5% based on the input penicillin acid); m. pt. and mixed m. pt. 145° – 146° with an authentic sample of the ester.

The bicarbonate wash was treated and acidified as described in Example 4 to yield 2.08 m.moles of the input acid.

Allowing for recovered acid gave a corrected yield of 81.5% ester based on the acid actually consumed.

EXAMPLE 4

2-Furylmethyl 3-acetoxymethyl-7β-(2-thienylacetamido) ceph-3-em-4-carboxylate To a solution of 3-acetoxymethyl-7β-(2-thienylacetamido) ceph-3-em-4-carboxylic acid (3.96 g, 10 m.moles) in acetonitrile (50 ml) and dimethylacetamide (15 ml) was added furfurylamine (0.97 g, 12 m.moles) and isopropyl nitrite (2.4 g, 27 m.moles) dissolved in acetonitrile (10 ml) at 35°. The slurry was maintained at 35° with stirring for 2 hours, a solution forming after the first hour. After removal of the solvents in vacuo the ethyl acetate solution (50 ml) of the residue was washed with 5% sodium bicarbonate (50 ml) and then water (200 ml). The partially solid organic residue on evaporation of the solvent was crystallised from isopropanol (100 ml) to yield the previously unreported title ester (2.19 g; 4.6 m.moles, 46% yield) m. pt. 161°. An analytical sample of the ester crystallised from methanol had m. pt. 163°; ν max (1% CHBr$_3$ solution) 3370 (—NHCO—), 1772 (β-lactam), 1730 + 1120 (acetate), 1720 (αβ-unsaturated ester), 1672 + 1502 cm$^{-1}$ (amide carbonyl); τ (10% CDCl$_3$) 2.65 – 3.10 (multiplet, thienyl ring), 6.17 (singlet, thienyl methylene acetamido group H$_2$), 3.55 (doublet, J 9 Hz, amide nitrogen proton H), 4.19 (double doublet, J 9, 5 Hz, C-7 H), 5.05 (doublet, J 5 Hz, C-6 H), 6.38, 6.72 (two doublets [branches of a quartet], J 18 Hz, C-2 H$_2$), 4.90, 5.22 (two doublets [branches of a quartet], J 14 Hz, 3-acetoxy methyl), 7.97 (singlet, 3-acetoxymethyl H$_3$), 4.75 (singlet, furylmethyl group H$_2$), 2.57 (multiplet, 5-furyl H) and 3.45 – 3.70 (multiplet, 3,4-furyl H$_2$). Found C, 53.1; H 4.3; N 5.7. C$_{21}$H$_{20}$N$_2$O$_7$S$_2$ requires C, 52.9; H, 4.2; N 5.9%.

Acidification of the bicarbonate extract yielded the starting material acid (1.27 g, 3.11 m.moles) m. pt 149.5° thus giving a corrected yield of 66.8% based on the acid actually consumed.

EXAMPLE 5

Cyclohexyl 3-acetoxymethyl-7β-(2-thienylacetamido)ceph-3-em-4-carboxylate

To a solution of 3-acetoxymethyl-7β-(2-thienylacetamido)ceph-3-em-4-carboxylic acid (3.96 g, 10 m.moles) in acetonitrile (50 ml) and dimethylacetamide (5 ml) was added a solution of isobutyl nitrite (2.47 g, 24 m.moles) and cyclohexylamine (1.20 g, 12 m.moles) in acetonitrile (20 ml). The resulting slurry was stirred at 45° for 2 hours, followed by the addition of extra dimethylacetamide (15 ml) and stirring for 17 hours at 35°. To the organic residue after evaporation of the solution solvent was added ethyl acetate (50 ml) and the organic layer washed with 5% sodium bicarbonate solution (40 ml) and water (50 ml). The organic residue was crystallised from isopropanol (25 ml) to yield the previously unreported title ester (1.10 g, 2.29 m.moles, 22.9% yield), m. pt. 165°–166°. An analytical sample of the ester had m. pt. 169°; ν max (1% CHBr$_3$ solution) 3420 (—NHCO—), 1790 (β-lactam), 1740 + 1245 (acetate), 1725 + 1228 (αβ-unsaturated ester), 1686 + 1515 cm$^{-1}$ (amide carbonyl); τ (5% CDCl$_3$) 7.95 (singlet, 3-acetoxymethyl), 6.38, 6.73 (two doublets [branches of a quartet], J 18 Hz), 6.18 (singlet, thienyl methylene acetamido grouping), 4.88, 5.22 (two doublets [branches of a quartet], J 14 Hz), 4.18 (double doublet, J 9, 5 Hz, C-7), 5.05 (doublet, J 5 Hz, C-6), 3.52 (doublet, amide nitrogen proton), 2.67–3.03 (multiplet, thienyl ring) and 8.0–8.80 (envelope, cyclohexyl). Found C, 55.4; H, 5.5; N, 5.6. C$_{22}$H$_{26}$N$_2$O$_6$S$_2$ requires C, 55.2; H, 5.5; N, 5.9%.

Acidification of the bicarbonate extract yielded the starting material acid (2.24 g, 5.64 m.moles) m. pt. 149° thus giving a corrected yield of 52.6% based on the acid actually consumed.

EXAMPLE 6

Diphenylmethyl 6β-phenylacetamido-2,2-dimethylpenam-3α-carboxylate 1β-oxide

6β-Phenylacetamido-2,2-dimethylpenam-3α-carboxylic acid 1β-oxide (3.50 g., 10 m. moles) was heated with diphenylmethylamine (2.21 g., 12 m. moles) and isopropyl nitrate (2.14 g., 24 m. moles) in dioxan (50 ml) at 35° over 6 hours. The solvent was removed in vacuo, replaced by ethyl acetate (50 ml) and the reaction mixture washed as described in Example 1. Crystallisation from hot isopropanol (25ml) of the gum left after evaporation of the organic solvent yielded the title ester (3.85 g., 74.6% based on the input acid), pure by t.l.c.

Acidification of the bicarbonate extract yielded the starting material acid (2.08 m. moles) thus giving a corrected yield of ester of 94.2% based on the acid actually consumed.

EXAMPLE 7

Benzyl 3-acetoxymethyl-7β-(2-thienylacetamido)ceph-3-em-4-carboxylate

To a solution of 3-acetoxymethyl-7β-(2-thienylacetamido) ceph-3-em-4-carboxylic acid (3.96 g., 10 m. moles) in acetonitrile (70 ml) and dimethylacetamide (5 ml) was added benzylamine (1.28 g., 12 m.

moles) and isobutyl nitrite (2.47 g., 24 m. moles) and the mixture heated to 45° over 2 hours. Initially a solid formed in the mixture but with vigorous stirring it had all dissolved after 1–1.25 hours as the reaction proceeded. After removal of the solvent in vacuo, the gum was taken up in ethyl acetate (50 ml) washed with dilute $H_2SO_4$(25 ml.), 5% $NaHCO_3$ solution (50 ml.) and water (50 ml.), and the organic residue after evaporation of the organic solvent crystallised from hot isopropanol to yield the title ester (2.40 g., 42% based on the input acid) m.pt. 135° – 139°. T.l.c. indicated the presence of some trace impurities.

Acidification of the bicarbonate extract yielded the starting material acid (1.85 g., 4.67 m. moles) thus giving a corrected yield of ester of 78.8% based on the acid actually consumed.

EXAMPLE 8

Diphenylmethyl 3-methyl-7β-phenoxyacetamidoceph-3-em-4-carboxylate

3-Methyl-7β-phenoxyacetamido ceph-3-em-4-carboxylic acid (3.48 g., 10 m. moles), diphenylmethylamine (3.20 g., 17.5 m. moles) and isopropyl nitrite (3.12 g., 35 m. moles) were heated at 35° over 2 hours in acetonitrile (50 ml). The solvent was removed in vacuo, replaced by ethyl acetate (50 ml) and washed as described in example 7. The organic residue was crystallised from hot isopropanol (30 ml) to yield the title ester (4.25 g., 82.6% based on the input acid) m.pt. 155°, pure by t.l.c.

EXAMPLE 9

9-Fluorenyl 3-methyl-7β-phenoxyacetamidoceph-3-em-4-carboxylate

3-Methyl-7β-phenoxyacetamidoceph-3-em-4-carboxylic acid (3.48 g., 10 m. moles) was dissolved with 9-aminofluorene (17.5 m moles) in dichloromethane (50 ml) together with isobutyl nitrite (3.62 g., 35 m. moles) and warmed at 35° for 18 hours. The reaction mixture was worked up as described in Example 7 except that a small quantity of ester (0.24, 0.48 m. moles) was filtered from the solution after the acid aqueous wash. On removal of the solvent the crystalline ester was slurried with warm isopropanol (50 ml), cooled and filtered to give the previously unreported title compound (2.60 g) m.pt. 214°, pure by t.l.c. Together with the previously filtered solid the weight of ester isolated represents a 56.8% yield based on the input acid. An analytical sample of the ester crystallised from acetone-methanol had m.pt. 221°– 222.5°; $\nu$ max (1% $CHBr_3$ solution) 3390 (—NHCO—), 1778 (β-lactam) 1718 (αβ-unsaturated ester), 1688 + 1520 $cm^{-1}$ (amide carbonyl); $\tau$ (8% $CDCl_3$ solution) 2.2 – 3.2 (complex, phenoxy ring + (—NHCO—) + fluorenyl 9-C + fluorenyl ring), 5.47 (singlet, phenoxy methylene acetamido group, $H_2$), 4.20 (doublet of doublets, J 10, 5 Hz, C-7, H), 5.04 (doublet, J 5 Hz, C-6, H), 6.45 + 6.89 (two doublets [branches of a quartet], J 18 Hz, $H_2$), 7.84 (singlet, C-3, $H_3$). Found C, 67.68; H, 4.64; N, 5.47. $C_{29}H_{24}N_2O_5S$ requires C, 67.97; H, 4.72; N, 5.47%.

Acidification of the bicarbonate extract yielded the starting material acid (0.37 g., 1.05 m. moles) thus giving a corrected yield of ester of 63.5% based on the acid actually consumed.

EXAMPLE 10

Triphenylmethyl 3-methyl-7β-phenoxyacetamidoceph-3-em-4-carboxylate

To 3-methyl-7β-phenoxyacetamidoceph-3-em-4-carboxylic acid (3.43 g., 9.5 m. moles) in dichloromethane (50 ml) was added triphenylmethylamine (4.3 g., 16.6 m. moles), isobutyl nitrite (3.43 g., 33.2 m. moles) and anhydrous sodium sulphate (5 g) and the mixture heated 2 hours at 35°. The cooled solution was washed with 5% sodium bicarbontae (30 ml) and water (30 ml). The organic solution was evaporated to a solid, the solid slurried in toluene (40 ml) cooled, filtered and slurry-washed with cold toluene (15 ml) to yield the previously unreported title compound (2.88 g. 50.0% yield based on the input acid) m.pt. 182°, pure by t.l.c. The compound possessed $\nu$ max (1% $CHBr_3$ solution) 3380 (NHCO), 1775 (β-lactam), 1723 (αβ-unsaturated ester) 1686 – 1518 $Cm^{-1}$ (amide carbonyl); $\tau$ (11% $CDCl_3$ solution) 2.2 – 3.2 (complex, phenyl rings + phenoxy ring + —NH), 5.41 (singlet, phenoxy methylene acetamido group, $H_2$), 4.09 (doublet of doublets J 4.5, 9 Hz, C-7, H) 4.95 (doublet, J 4.5 Hz, H), 6.51 + 6.97 (two doublets [branches of a quartet]J 18 Hz, $H_2$), 8.08 (singlet, C-3, $H_3$). Found C, 70.63; H, 5.16 N, 4.52. $C_{35}H_{30}N_2O_5S$ requires C, 71.18; H, 5.09; N, 4.75%.

Acidification of the bicarbonate extract yielded the starting material acid (1.25 g., 3.60 m. moles ) thus giving a corrected yield of ester of 84.8% based on the acid actually consumed.

EXAMPLE 11

Diphenylmethyl 6β-phenylacetamido-2,2-dimethylpenam-3α-carboxylate 1β-oxide

6β-Phenylacetamido-2,2-dimethylpenam-3α-carboxylic acid 1β-oxide (3.50 g., 10 m. moles) was dissolved with diphenylmethylamine (3.22 g., 17.5 m. moles) and tertbutyl nitrite (3.60 g., 35 m.moles) in 1,2-dichloroethane (50 ml) and heated at 45° over 2 hours. The cooled reaction mixture was worked up as described in Example 7 and the organic residue crystallised from isopropanol (35 ml), washed with chilled isopropanol (25 ml) to yield the title ester (4.75 g., 92% based on the input penicillin acid) m.pt. 126° – 127°. T.l.c. indicated the presence of a trace impurity.

EXAMPLE 12

Diphenylmethyl 3-acetoxymethyl-7β-(2-thienylacetamido) ceph-3-em-4-carboxylate 3-Acetoxymethyl-7β-(2-thienylacetamido) ceph-3-em-4-carboxylic acid (3.96 g., 10 m. moles) was dissolved in a mixture of 1,2-dichloroethane (40 ml) and dimethylacetamide (3.5 ml). To this solution was added pyridine (1.78 g., 20 m. moles) and diphenylmethylamine (3.66 g., 20 m. moles), whereafter some solid separated out. To this mixture at −30° was added nitrosyl chloride (0.92 ml, 20 m. moles in 1,2-dichloroethane (15 ml) whereupon gas was evolved and the solution turned yellow through green. The solids gradually dissolved during the course of three hours as the temperature rose slowly to ambient. The reaction mixture was washed with dilute sulphuric acid (20 ml), 5% sodium bicarbonate solution (50 ml) and water (50 ml) and the organic residue crystallised from isopropyl alcohol (25 ml) to yield the title ester (1.39 g., 2.47 m. moles, 24.7% yield) m.pt. 142°.

Acidification of the bicarbonate solution yielded the starting material acid (2.68 g., 6.78 m. moles) m.pt. 144° thus giving a corrected yield of ester of 76.6% based on the acid actually consumed.

EXAMPLE 13

Diphenylmethyl D-(−)-N-(2,2,2-trichloroethyoxycarbonyl)-2-phenylglycinate

To dichloromethane (50 ml) was added D-(−)-N-(2,2,2-trichloroethoxy carbonyl-2-phenylglycine (2.25 g., 10 m. moles), diphenylmethylamine (4.58 g., 25 m. moles), anhydrous sodium sulphate (5 g) and potassium carbonate (6.7 g). Nitrosyl chloride (12.5 ml, 10% solution in dichloromethane 25 m. moles) was added over 10 minutes at −5° with vigorous stirring. The mixture was allowed to warm towards ambient over 50 minutes and water (80 ml) added. The solid was filtered, and the organic solvent washed with 1N sulphuric acid (20 ml) and water (50 ml). The semi-solid remaining after evaporation of the solvent was triturated with ether (50 ml) and the now-clean solid combined with the previously filtered solid, slurry washed with ether (30 ml) and filtered to give the title ester (3.33 g., 85.4% based on the input acid) m.pt. 176°, pure by t.l.c.

EXAMPLE 14

Diphenylmethyl 6β-phenylacetamido-2,2-dimethylpenam-3α-carboxylate 1β-oxide

6β-Phenylacetamido-2,2-dimethylpenam-3α-carboxylic acid 1β-oxide (3.50 g., 10 m.moles) was added to dichloromethane (50 ml) containing diphenylmethylamine (4.77 g., 25 m. moles), anhydrous sodium sulphate (5 g) and potassium carbonate (6.7 g). Nitrosyl chloride (12.5 ml, 10% solution in dichloromethane 25 m. moles) was added over 10 minutes with vigorous stirring at −5° after the addition the reaction was allowed to warm towards ambient over 50 minutes. The mixture was worked up as described in Example 7 and the organic residue crystallised from hot isopropanol (25 ml) to yield the title ester (4.45 g., 86.2% based on the input penicillin acid) m.pt. 146°, pure by t.l.c.

Acidification of the alkaline extract yielded the starting material acid (0.48 m. moles) thus giving a corrected yield of 90.5% based on the acid actually consumed.

EXAMPLE 15 p-Methoxybenzyl 3-methyl-7β-phenoxyacetamidoceph-3-em-4-carboxylate

3-Methyl-7β-phenoxyacetamidoceph-3-em-4-carboxylic acid (3.48 g., 10 m. moles) was dissolved in dichloromethane (50 ml) with p-methoxy-benzylamine (3.43 g., 25 m. moles) together with anhydrous sodium sulphate (5 g) and potassium carbonate (6.7 g). Nitrosyl chloride (12.5 ml, 10% solution in dichloromethane, 25 m. moles) was added over about 10 minutes at −5° with vigorous stirring. Some partial gel formation occurred but this dissolved while the mixture was stirred for a further 50 minutes while warming towards ambient. The reaction mixture was worked up as described in Example 7 and the organic residue crystallised from hot isopropanol (25 ml) to give the title compound (2.38 g., 50.6% yield based on the input acid) m.pt. 151° − 152°.

Acidification of the alkaline extract gave the starting material acid (1.37 g., 3.94 m. moles) thus giving a corrected yield of 83.5% based on the acid actually consumed.

EXAMPLE 16 p-Nitrobenzyl 3-methyl-7β-phenoxyacetamidoceph-3-em-4-carboxylate

3-Methyl-7β-phenoxyacetamidoceph-3-em-4-carboxylic acid (3.28 g., 9.42 m. moles) was dissolved in dichloromethane (50 ml) with p-nitrobenzylamine (25 m. moles) together with potassium carbonate (6.7 g) and anhydrous sodium sulphate (5 g). Nitrosyl chloride (12.5 ml, 10% solution in dichloromethane, 25 m. moles) was added over about 10 minutes with vigorous stirring at −5° and after the addition the mixture was allowed to warm towards room temperature over 50 minutes. The reaction mixture was worked up as described in Example 7 and the residue crystallised from methanol (25 ml) to yield the title ester (0.78 g., 17.9% based on the input acid) m.pt. 176° − 181°.

Acidification of the alkaline extract yielded the starting material acid (2.56 g., 7.35 m. moles) thus giving a corrected yield of 82.2% based on the acid actually consumed.

We claim:

1. In a process for the preparation of an ester of an N-blocked amino acid, wherein said N-blocked amino acid is a penicillin, the improvement which comprises reacting an N-blocked penicillin acid, or a salt thereof formed from an alkali metal with an amine of the formla $RNH_2$, where R is a member selected from the group consisting of a $C_{5-7}$ cycloalkyl, benzyl, diphenylmethyl, triphenylmethyl, fluoroenyl, xanthydryl, thienylmethyl and furylmethyl and such a group substituted by at least one of chloro, bromo, cyano, nitro, $C_{1-6}$ alkyl, $C_{1-6}$ alkoxy, $C_{2-7}$ alkoxycarbonyl and $C_{1-6}$ alkylsulphonyl, and a nitrosating agent selected from the group consisting of $C_{2-7}$ alkanoyl nitrites, nitrosyl chloride, nitrosyl bromide, nitrosyl sulphate, nitrosyl hydroxide, nitrosyl sulphonate, nitrosyl borofluoride, nitrous acid, potassium nitrosyldisulphonate and $C_{1-9}$ alkyl nitrites, to yield an N-blocked amino acid ester in which the ester group has the formula —COOR where R is as defined above.

2. A process as claimed in claim 1 wherein R is a diphenylmethyl, benzyl, triphenylmethyl, 2-thienylmethyl or 2-furylmethyl group.

3. A process as claimed in claim 1 wherein the nitrosating agent is nitrosyl chloride or isopropyl nitrite.

4. A process as claimed in claim 1 which is effected at a temperature of −30° to +100°c.

5. A process as claimed in claim 1, wherein the esterification is effected in an organic solvent or in a mixture of solvents.

6. A process as claimed in claim 1, wherein the nitrosating agent is an alkyl nitrite, said nitrite being present at a concentration of about 3.5 moles/mole of N-blocked amino acid and the amine is present in the concentration of about 1.75 moles of amine per mole of N-blocked amino acid.

* * * * *